US00PP17498P2

(12) United States Plant Patent
Verheijen

(10) Patent No.: US PP17,498 P2
(45) Date of Patent: Mar. 13, 2007

(54) ***HYPERICUM* PLANT NAMED 'VEROCLA'**

(50) Latin Name: *Hypericum androsaemum*
Varietal Denomination: Verocla

(75) Inventor: Edwin Martijn Verheijen, Wieringerwerf (NL)

(73) Assignee: Handelskwekerij, Wieringewerf (NL)

( * ) Notice: Subject to any disclaimer, the term of this patent is extended or adjusted under 35 U.S.C. 154(b) by 18 days.

(21) Appl. No.: 11/177,974

(22) Filed: Jul. 8, 2005

(51) Int. Cl.
*A01H 5/00* (2006.01)

(52) U.S. Cl. ..... Plt./226
(58) Field of Classification Search ..... Plt./226
See application file for complete search history.

*Primary Examiner*—Anne Marie Grunberg
*Assistant Examiner*—S. B. McCormick-Ewoldt
(74) *Attorney, Agent, or Firm*—C. A. Whealy

(57) ABSTRACT

A new and distinct cultivar of *Hypericum* plant named 'Verocla', characterized by its upright plant habit; durable dark green-colored leaves; bright light green-colored fruits; and good postproduction longevity.

2 Drawing Sheets

Botanical designation: *Hypericum androsaemum.*
Cultivar denomination: 'Verocla'.

BACKGROUND OF THE INVENTION

The present Invention relates to a new and distinct cultivar of *Hypericum* plant, botanically known as *Hypericum androsaemum,* commercially used as cut stems with fruits, and hereinafter referred to by the name 'Verocla'.

The new *Hypericum* is a product of a planned breeding program conducted by the Inventor in Wieringerwerf, The Netherlands. The objective of the breeding program was to develop cut *Hypericum* varieties with attractive fruit coloration.

The new cultivar originated from a cross-pollination made by the Inventor in January, 2000 of a proprietary selection of *Hypericum* identified as code number A20345, not patented, as the female, or seed, parent with a proprietary selection of *Hypericum* identified as code number 121346, not patented, as the male, or pollen, parent. The cultivar Verocla was discovered and selected by the Inventor during the summer of 2001 as a flowering plant within the progeny of the stated cross-pollination in a controlled environment in Wieringerwerf, The Netherlands.

Asexual reproduction of the new *Hypericum* by terminal cuttings at Wieringerwerf, The Netherlands since September, 2001, has shown that the unique features of this new *Hypericum* are stable and reproduced true to type in successive generations of asexual reproduction.

SUMMARY OF THE INVENTION

The following traits have been repeatedly observed and are determined to be the unique characteristics of 'Verocla'. These characteristics in combination distinguish 'Verocla' as a new and distinct cultivar:

1. Upright plant habit.
2. Durable dark green-colored leaves.
3. Bright light green-colored fruits.
4. Good postproduction longevity.

Plants of the new *Hypericum* differ from plants of the female parent selection in the following characteristics:

1. Plants of the new *Hypericum* have longer flowering stems than plants of the female parent selection.
2. Plants of the new *Hypericum* have smaller fruits than plants of the female parent selection.
3. Plants of new *Hypericum* and the female parent selection differ in fruit coloration as plants of the female parent selection have brown-colored fruits.

Plants of the new *Hypericum* differ from plants of the male parent selection in the following characteristics:

1. Plants of the new *Hypericum* have longer flowering stems than plants of the male parent selection.
2. Plants of the new *Hypericum* have more durable leaves than plants of the male parent selection.
3. Plants of the new *Hypericum* have fewer flowers per inflorescence than plants of the male parent selection.
4. Plants of the new *Hypericum* and the male parent selection differ in fruit coloration as plants of the male parent selection have red-colored fruits.

Plants of the new *Hypericum* can be compared to plants of the *Hypericum* cultivar Excellent Flair, not patented. In side-by-side comparisons conducted in Wieringerwerf, The Netherlands, plants of the new *Hypericum* differed from plants of the cultivar Excellent Flair in the following characteristics:

1. Plants of the new *Hypericum* had shorter, darker green and more durable leaves than plants of the cultivar Excellent Flair.
2. Plants of the new *Hypericum* had smaller flowers than plants of the cultivar Excellent Flair.
3. Plants of the new *Hypericum* had thicker and stronger flowering stems than plants of the cultivar Excellent Flair.
4. Fruits of plants of the new *Hypericum* were bright light green in color whereas fruits of plants of the cultivar Excellent Flair were brownish red in color.

BRIEF DESCRIPTION OF THE PHOTOGRAPHS

The accompanying colored photographs illustrate the overall appearance of the new *Hypericum,* showing the colors as true as it is reasonably possible to obtain in colored reproductions of this type. Colors in the photographs may differ slightly from the color values cited in the detailed botanical description which accurately describe the colors of the new *Hypericum*.

The photograph on the first sheet comprises a side perspective view of a typical flowering stem of 'Verocla' with developed fruit.

The photograph at the top of the second sheet is a close-up view of typical fruits of 'Verocla'.

The photograph at the bottom of the second sheet is a close-up view of typical flowers of 'Verocla'.

DETAILED BOTANICAL DESCRIPTION

The new *Hypericum* has not been observed under all possible environmental conditions. The phenotype may vary somewhat with variations in environment such as temperature and light intensity, without, however, any variance in genotype.

The aforementioned photographs, following observations and measurements describe plants grown in Tabacundo, Ecuador, in an outdoor nursery and under commercial production practices. Plants used for the photographs and the description were about one year old. The photographs and description were taken in March with day temperatures averaging 17° C., night temperatures averaging 10° C. and light levels ranging from 800 to 1,100 watts per square meter. In the following description, color references are made to The Royal Horticultural Society Colour Chart, 1995 Edition, except where general terms of ordinary dictionary significance are used.

Botanical classification: *Hypericum androsaemum* cultivar Verocla.

Parentage:

*Female parent.*—Proprietary selection of *Hypericum androsaemum* identified as code number A20345, not patented.

*Male parent.*—Proprietary selection of *Hypericum androsaemum* identified as code number 121346, not patented.

Propagation:

*Type.*—Terminal cuttings.

*Time to initiate roots, summer.*—About two weeks at 20° C.

*Time to initiate roots, winter.*—About three weeks at 20° C.

*Time to produce a rooted cutting, summer.*—About 30 days at 20° C.

*Time to produce a rooted cutting, winter.*—About 40 days at 20° C.

*Root description.*—Fine, fibrous; brown, 165B overlain with 200A, in color.

*Rooting habit.*—Freely branching; dense.

Plant description:

*Plant form.*—Upright and somewhat outwardly spreading perennial woody shrub.

*Growth habit.*—Moderately vigorous. Freely basal branching; dense and bushy growth habit.

*Plant height.*—About 70 cm.

*Plant width (spread).*—About 40 cm.

*Quantity of stems per year.*—About eight.

*Lateral branches.*—Length: About 10 cm. Diameter: About 2.3 mm. Internode length: About 4.2 cm. Strength: Moderately strong. Texture: Smooth; glabrous. Color: 145D.

*Foliage description.*—Arrangement: Opposite; simple; sessile. Length: About 6.3 cm. Width: About 5.1 cm. Shape: Ovate. Apex: Slightly retuse. Base: Obtuse to slightly cordate. Margin: Entire. Texture, upper and lower surfaces: Glabrous; rugose. Venation pattern: Pinnate. Color: Developing leaves, upper surface: 144A. Developing leaves, lower surface: 147D. Fully expanded leaves, upper surface: Darker than 147A; venation, 145B. Fully expanded leaves, lower surface: 147C; venation, 145C. Stipule length: About 6 mm. Stipule diameter: About 3 mm. Stipule texture, upper and lower surfaces: Smooth, glabrous. Color, upper surface: 144A. Color, lower surface: 147D.

Flower description:

*Flower type and habit.*—Bright yellow single flowers arranged in terminal compound umbels with about twelve flowers per umbel. Flowers not fragrant. Flowers persistent. Flowers face upright to outwardly.

*Natural flowering season.*—Summer, typically June to September in The Netherlands.

*Postproduction longevity.*—Cut flower are typically harvested when all flowers have developed fruits. Postproduction longevity of cut stems with fruits is about two weeks.

*Inflorescence height.*—About 2.5 cm.

*Inflorescence diameter.*—About 7 cm.

*Flower buds.*—Height: About 7.6 mm. Diameter: About 7.6 mm. Shape: Rounded oblong. Color: 10B; towards the apex, 12A.

*Flowers.*—Diameter: About 2.6 cm. Depth: About 1.3 cm.

*Petals.*—Quantity per flower: Five. Length: About 1.2 cm. Width: About 9.7 mm. Shape: Obovate. Apex: Obtuse, cuspidate. Base: Attenuate. Margin: Entire. Aspect: Concave. Texture, upper and lower surfaces: Smooth; glabrous. Color: Developing and fully expanded petals, upper surface: 12A. Developing and fully expanded petals, lower surface: 12B to 12C.

*Sepals.*—Quantity per flower: Five. Length: About 9 mm. Width: About 8 mm. Shape: Broadly ovate. Apex: Obtuse to rounded. Base: Broadly attenuate. Margin: Entire. Texture, upper surface: Smooth; glabrous. Texture, lower surface: Slightly rugose; glabrous. Color: Developing sepals, upper surface: 144A. Developing sepals, lower surface: 145D. Fully expanded sepals, upper surface: 137B; towards the base, 144C. Fully expanded sepals, lower surface: 193B.

*Peduncles.*—Length: About 1.7 cm. Diameter: About 2 mm. Orientation: Erect to about 45° from vertical. Strength: Strong. Texture: Smooth, glabrous. Color: 145B.

*Pedicels.*—Length: About 2.4 cm. Diameter: About 1.4 mm. Orientation: Erect to about 45° from vertical. Strength: Moderately strong. Texture: Smooth, glabrous; slightly grooved. Color: 145B.

*Reproductive organs.*—Stamens: Quantity per flower: About 110. Anther shape: Broadly ovate. Anther length: About 0.8 mm. Anther color: 17C. Pollen amount: Moderate. Pollen color: 21A. Pistils: Quantity per flower: Three. Pistil length: About 1.2 cm. Stigma shape: Globular. Stigma color: 46A. Style length: About 5 mm. Style color: 154B. Ovary color: 154B.

*Fruits.*—Quantity per flower: One. Days to ripening: About 25. Type: Capsule. Shape: Roughly spherical. Length: About 1 cm. Diameter. About 1 cm. Texture: Smooth; glabrous. Color: 144C.

*Seeds.*—Quantity per fruit: More than 100. Length: About 1.3 mm. Diameter: About 0.6 mm. Texture: Smooth; glabrous. Color: 200B.

Disease/pest resistance: Plants of the new *Hypericum* have been observed to be resistant to Rust. Plants of the new *Hypericum* have not been observed to be resistant to pests and other pathogens common to *Hypericum*.

Temperature tolerance: Plants of the new *Hypericum* have been observed to tolerate temperatures ranging from −15 to 35° C.

It is claimed:

1. A new and distinct cultivar of *Hypericum* plant named 'Verocla', as illustrated and described.

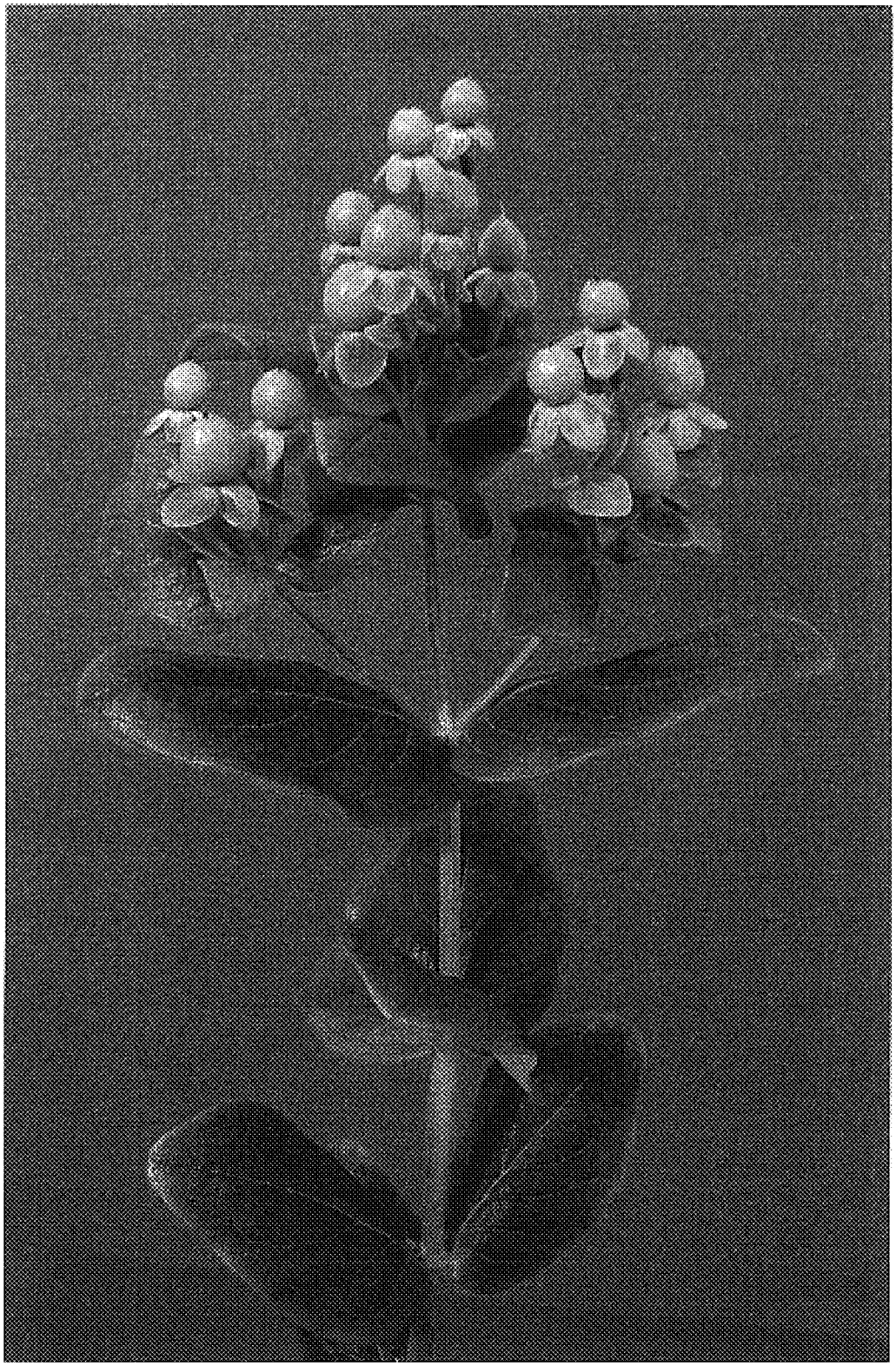

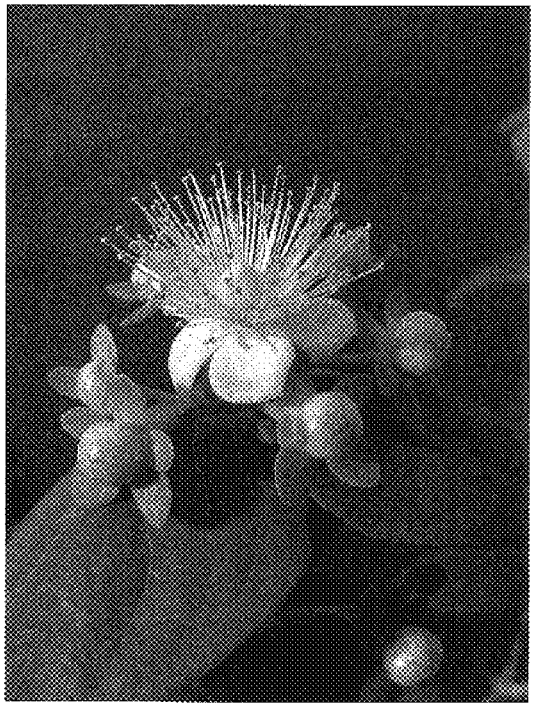
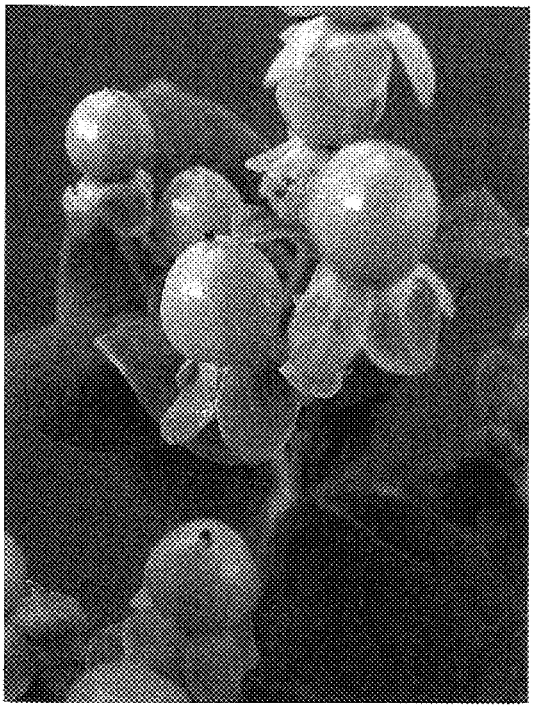

* * * * *